United States Patent [19]

Daly et al.

[11] 4,402,613
[45] Sep. 6, 1983

[54] SURFACE INSPECTION SYSTEM

[75] Inventors: John K. Daly, Scottsdale; Malvin D. Terry, Phoenix, both of Ariz.

[73] Assignee: Advanced Semiconductor Materials America, Phoenix, Ariz.

[21] Appl. No.: 24,944

[22] Filed: Mar. 29, 1979

[51] Int. Cl.³ .................. G01N 21/47; G01N 21/55; G01N 21/84; G01N 21/01
[52] U.S. Cl. .................. 356/446; 356/445; 356/430; 356/426; 356/244
[58] Field of Search .............. 356/445, 446, 430, 431, 356/426, 244; 250/562, 563, 548; 414/416

[56] References Cited

U.S. PATENT DOCUMENTS

| | | | |
|---|---|---|---|
| 3,790,287 | 2/1974 | Cuthbert et al. | 356/446 |
| 3,850,526 | 11/1974 | Corey | 356/445 |
| 3,890,508 | 6/1975 | Sharp | 250/548 |
| 3,902,615 | 9/1975 | Levy et al. | 414/416 |
| 4,037,970 | 7/1977 | Webster et al. | 356/446 X |
| 4,062,623 | 12/1977 | Suzuki et al. | 356/445 |
| 4,065,211 | 12/1977 | Vig | 356/30 X |
| 4,073,590 | 2/1978 | Brown | 356/446 X |
| 4,155,098 | 5/1979 | Roach et al. | 250/562 |
| 4,178,113 | 12/1979 | Beaver et al. | 414/416 |

Primary Examiner—John K. Corbin
Assistant Examiner—Rodney B. Bovernick
Attorney, Agent, or Firm—Harry M. Weiss

[57] ABSTRACT

A surface inspection system utilizes a laser light source, and a vacuum chuck to support the material whose surface is to be inspected. The vacuum chuck is rotatable. The laser beam may be translated across the work surface while the chuck is rotated, all the while maintaining mutual perpendicularity of the vacuum chuck work surface and the laser beam. An airtrack transports the material whose surface is to be inspected. Sensors are utilized to detect the position of such material along the track and to guide the system in its operation.

5 Claims, 13 Drawing Figures

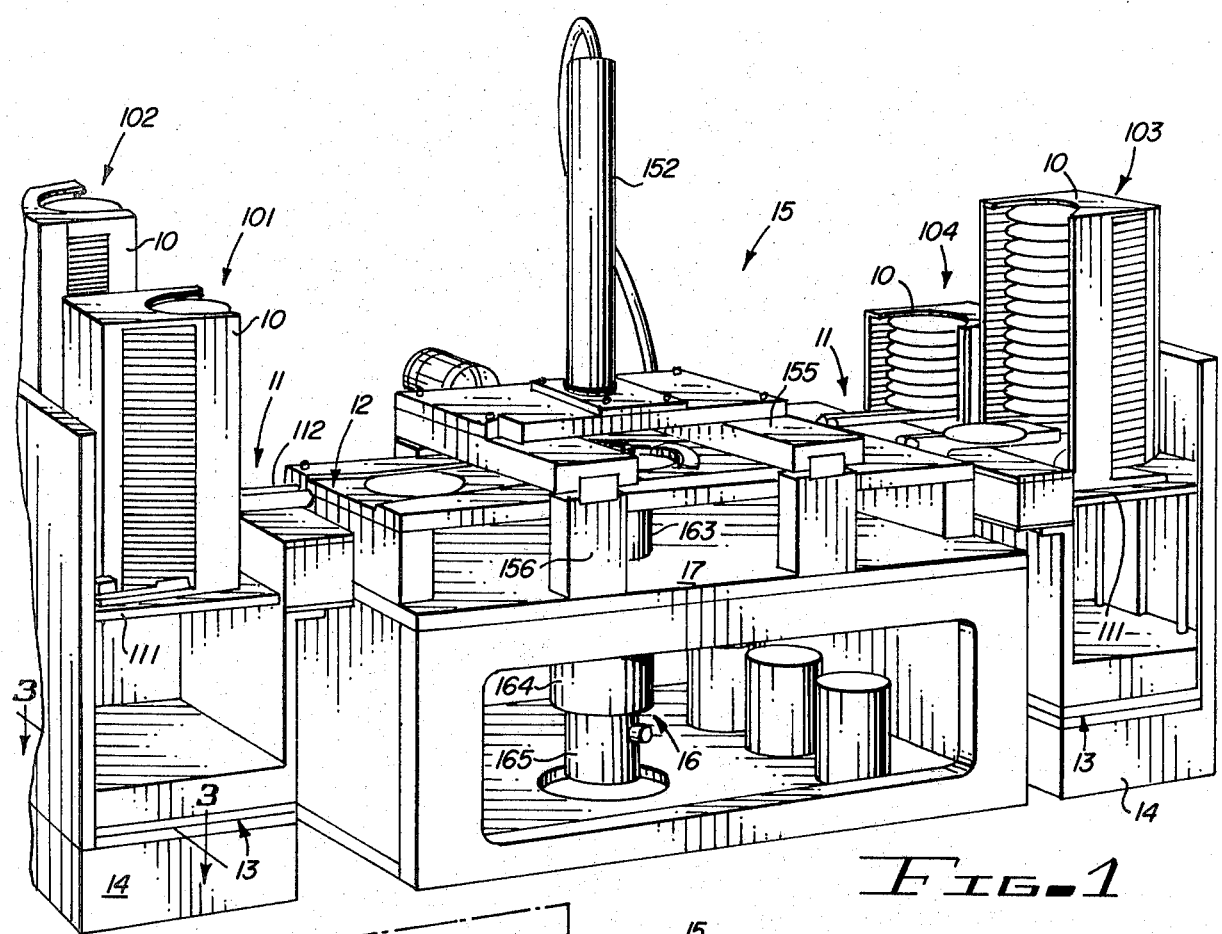
FIG-1
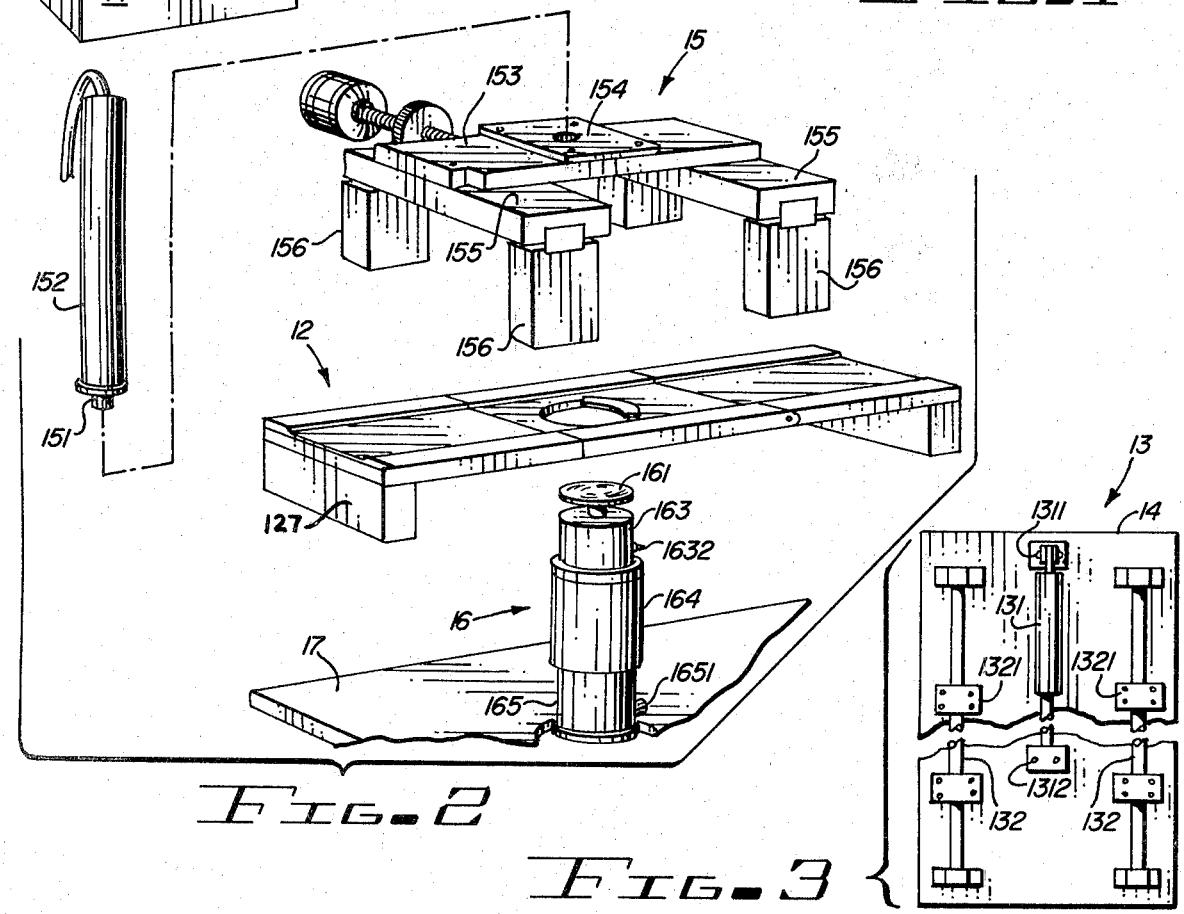
FIG-2
FIG-3

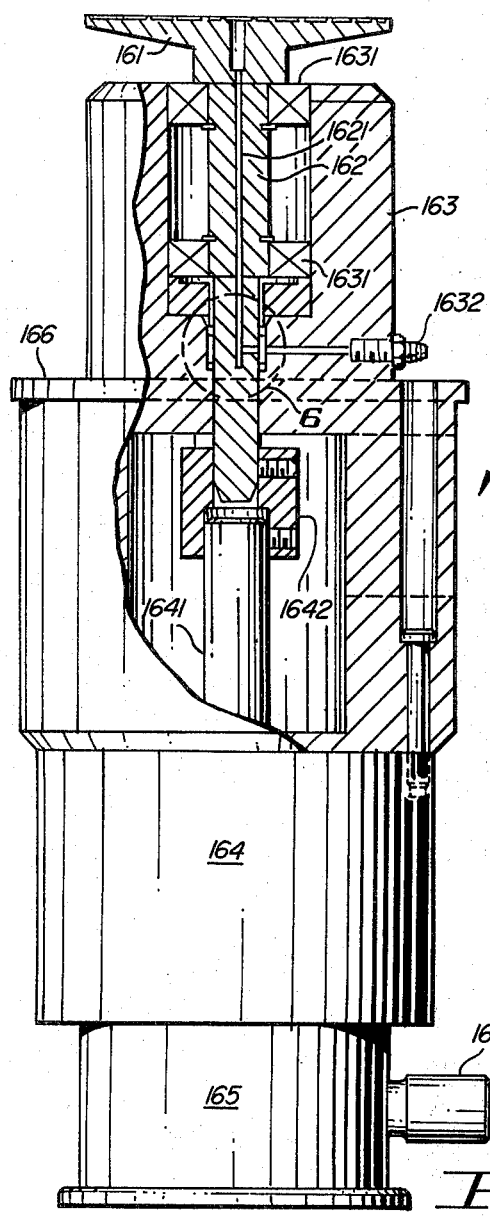
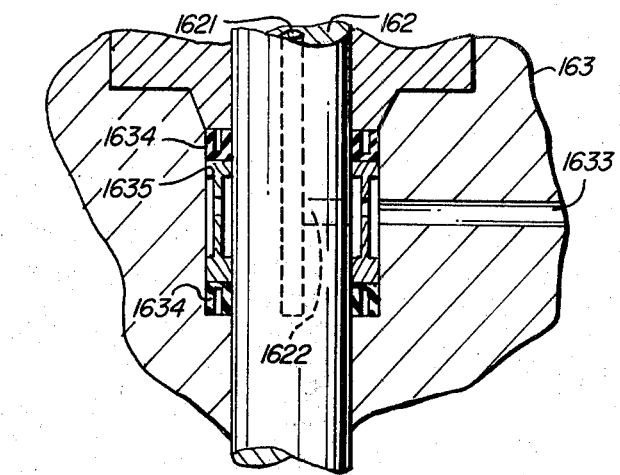
FIG.-6
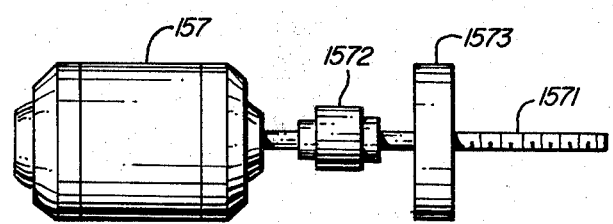
FIG.-4
FIG.-5
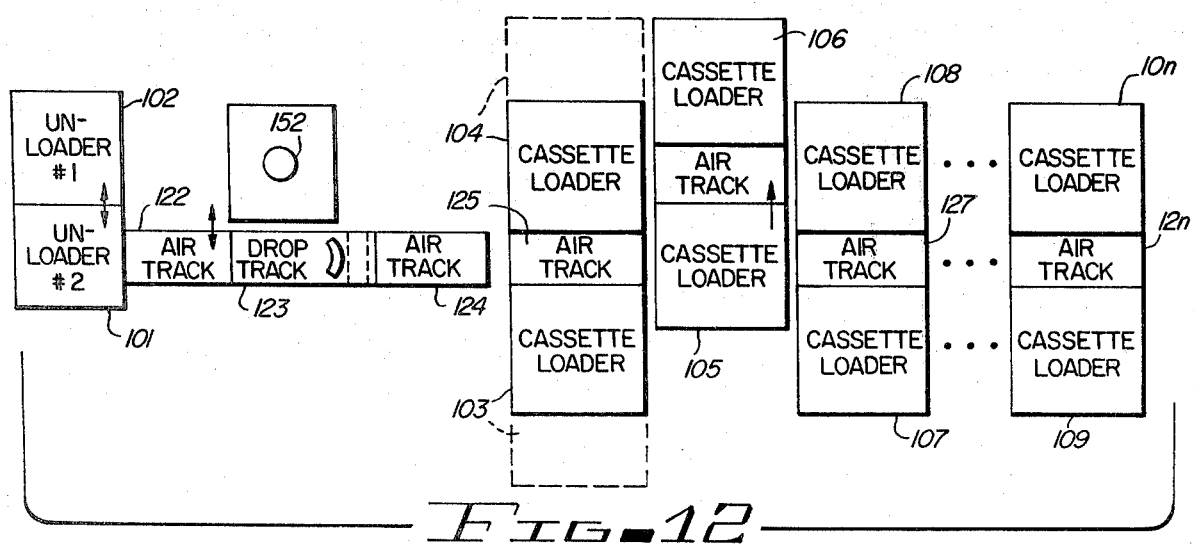
FIG.-12

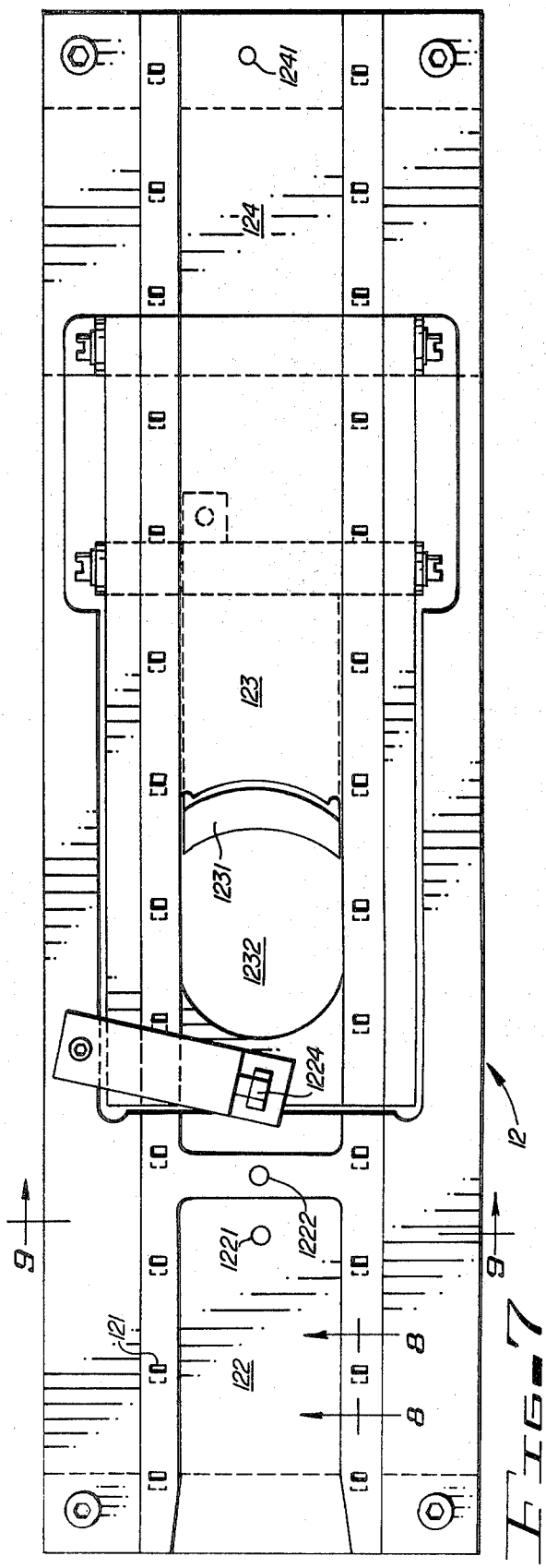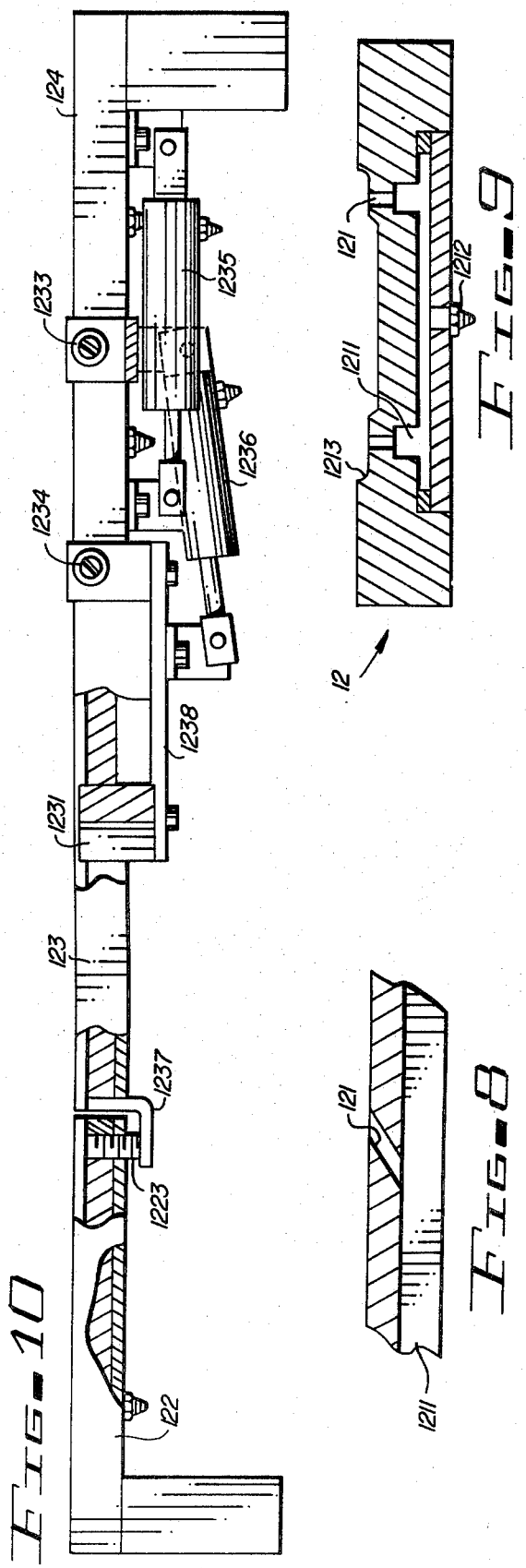

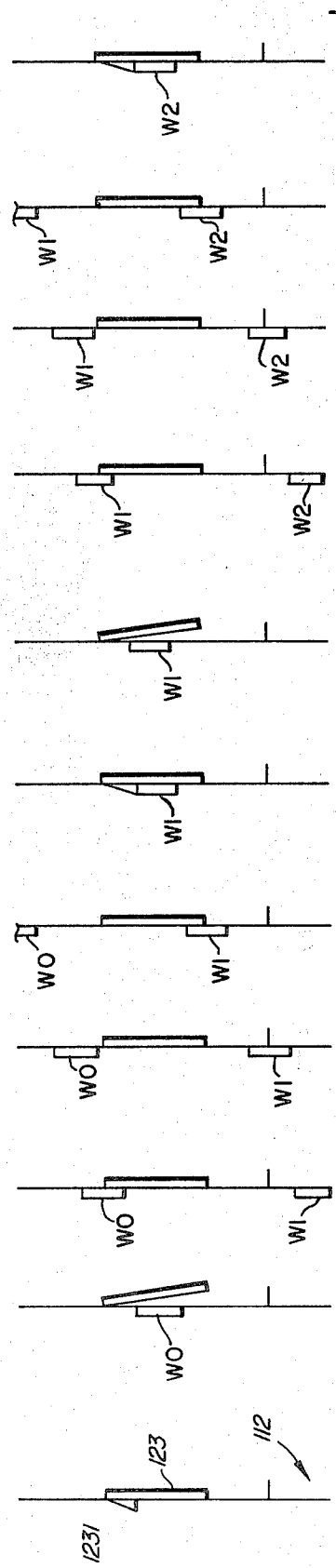
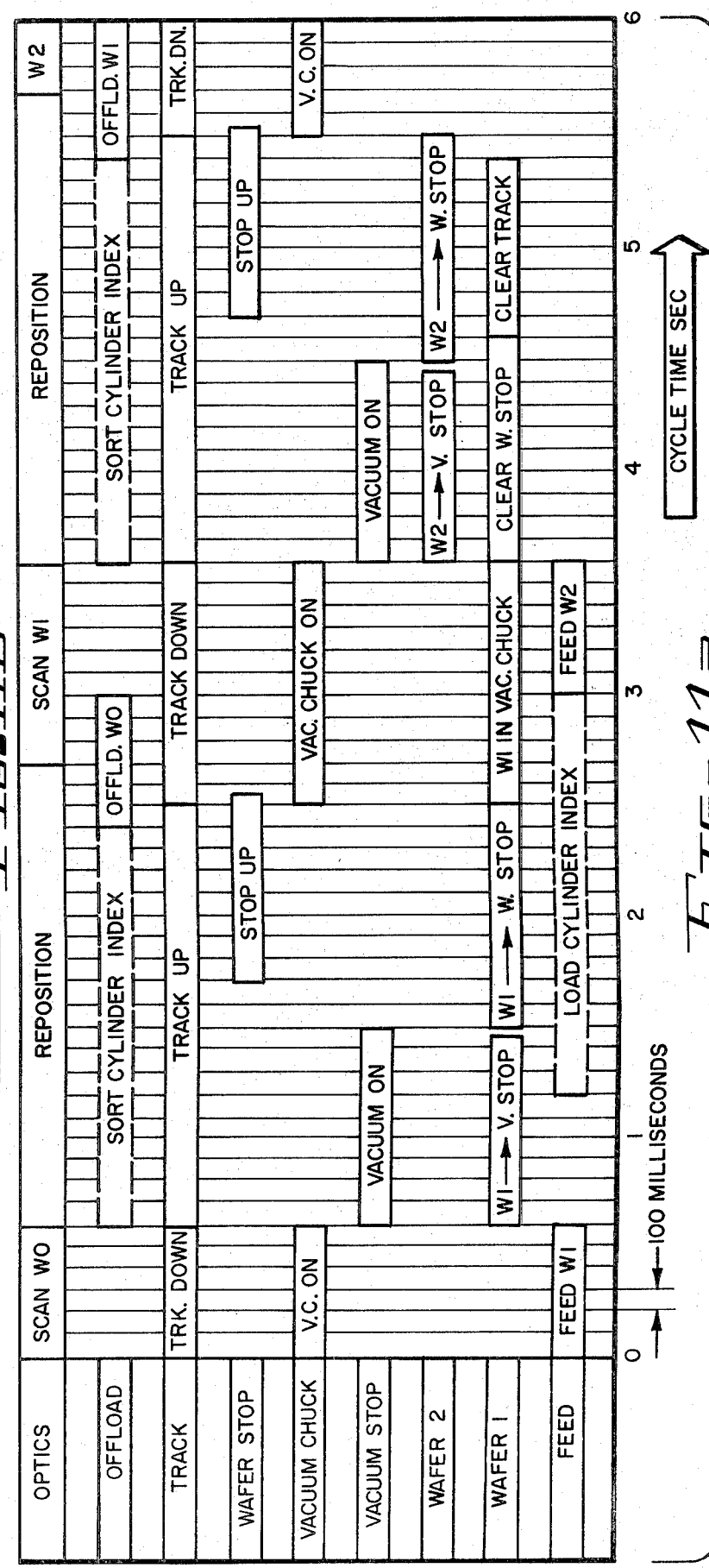
Fig-11b
Fig-11a

SURFACE INSPECTION SYSTEM

This invention relates to a surface measurement system using collimated light which impinges upon the surface to be measured and a detector which detects the light scattered by surface irregularities.

In another respect, the invention relates to a surface measuring system using a laser light source for measurements of surface irregularities on highly polished planar surfaces.

In still another respect, the invention relates to a surface inspection system for use with semiconductor wafers providing control means for transporting said wafers to the location at which the surface measurement is to be made and away from that site upon completion of said measurement.

In yet another respect, the invention relates to a scattered light, surface inspection system, utilizing a laser light source and a scattered light detector, which employs no reflective surfaces in the light path between the laser output, the surface to be measured, and the scattered light detector.

In particular, the invention relates to a surface inspection system which rotates a highly polished planar surface and simultaneously translates that surface relative to an impinging beam of collimated light such that the light beam scans the surface being measured so that the track of said beam on said surface describes an archimedes spiral.

The rapid advancement of growth of technology in the semiconductor field has affected the lives of everyone. Semiconductors are now found not only in equipment considered to be "electronic" in nature such as receivers and computer equipment, but they are finding themselves into everyday household items. Children's toys, the homeowner's tools, small appliances for use in kitchens, and the like may all be found today to contain some form of semiconductor either to control speed, provide guidance, or to program a whole sequence of operations. The art of providing high-quality process semiconductor material has grown apace with the technological innovations which lead to ever greater and varied usage of semiconductor devices.

Processed semiconductor materials of high quality, at reasonable costs, are required to support the burgeoning semiconductor industry. Manufacturing processes require tight quality control procedures which are highly efficient if the flow of processed semiconductor materials at reasonable prices is to be realized. The present invention is responsive to meeting the need of one such highly precise and efficient quality control procedure. The surface quality of semiconductor wafers being processed for use in semiconductor industries must be constantly monitored for defects introduced during the handling and processing of the wafers. The invention herein disclosed finds broad application during such semiconductor wafer processing in the areas of incoming/outgoing quality control, in-process quality assurance, polishing and cleaning process control, pre-oxidation and post-oxidation/photolithography/diffusion control, and pre/post epitaxial process control.

Semiconductor materials are provided to semiconductor device manufacturers in the form of wafers. Wafer sizes in the range of two to five inches are typical. A conventional thickness would be about 0.025 inches.

Surface quality of the wafers is a critical criterion which must be controlled if high-yield semiconductor devices are to be produced. It is not unusual to find semiconductor processors utilizing equipment capable of detecting surface defects in the planar, polished surface of a semiconductor wafer, which defects have physical dimensions on the order of one micron (the thousandth part of one millimeter). It is a challenge to utilize such precision equipment under the demands generated by a high production, controlled quality environment.

The concept of determining surface quality using scattered light techniques is old in the art. The principle relied upon is the familiar one that the angle at which light is incident on a smooth, planar surface is equal to the angle at which the light reflects from that surface. The proposition is often stated more succinctly as, "the angle of incidence equals the angle of reflection." A collimated light source is assumed. Since the angle of incidence and the angle of reflection are equal, it is readily seen that as the light approaches the surface from an incidence angle of 90°, the reflected light will leave the surface of the reflector and travel back along the path of the incident light. However, should a superficial anomaly appear on the surface at the point at which the light is incident, there will tend to be a scattering of the light as it strikes the anomaly and light will be reflected at various angles different from that at which the light is incident upon that portion of the surface having no such anomalies.

To understand the basic mechanism employed to detect surface defects, one should envision a light beam from a collimated light source. The beam passes through an aperture and is directed toward the surface to be inspected so as to be incident on that surface at an angle of 90°. If the surface is truly planar, light reflected from it will travel back along the path of incidence, passing back through the aperture opening as it does so. However, should the surface be defective in some way so as to cause scattering of the light as it impinges on the surface, the reflected light will be scattered and will not pass back through the aperture opening. Rather, some of the reflected light will strike the surface surrounding and supporting the aperture opening. The greater the surface anomaly, the greater will be the scattering of light upon reflection from that surface and the greater will be the amount of light which misses the aperture opening and strikes the surface surrounding and supporting that aperture. If that surface is comprised of a light sensor, then the magnitude of the output from that light sensor will quantitatively indicate the magnitude of the surface anomaly.

A laser is the most frequently used source of collimated light. The light is directed from the laser output via a series of prisms or reflective surfaces so as to impinge on the surface to be measured at the required 90° angle. The surface to be measured is then passed beneath the laser beam and the degree of light scattering determined. A major problem in devising such a system for measuring surface quality concerns the maintenance of the light beam and the surface to be measured at the critical 90° angle of incidence. The adjustment of the laser beam, the establishment of proper working angles for prisms and reflectors, and the control of the relative movement between laser beam and measured surface are all of major importance before the first measurement can be made. Maintaining these relationships over any period of time and use of the equipment present an almost insurmountable problem. In the processing of semiconductor materials surface quality is of prime importance. For economies of operation the semiconductor materials must pass smoothly and efficiently through the surface inspection devices so that cost effective production may be maintained.

It is an object of the present invention to provide a surface inspection system for the quantitative measurement of the defect level present on a highly reflective surface.

It is a further object of the invention that it should incorporate a highly sensitive solid-state detector to collect laser energy that has been scattered by defects such as surface haze, particles, scratches, fingerprints, moisture, hillocks, spikes, etc.

An additional object of the invention is to provide relative movement between a laser light beam and a surface to be measured so as to assure complete coverage of the surface in a reasonable time period.

An important objective of the invention is to provide a surface measuring system which provides for automatic handling of the surfaces to be measured.

Since the invention leads itself to use in the semiconductor processing industry, a preferred embodiment for use in that environment will be described. In summary description, the invention consists of a surface inspection system comprising handling means for the manual transport of semiconductor wafers, automated means for loading and unloading said handling means without manual assistance, a laser light source, a scattered light detector, means for moving the laser, means for moving semiconductor material while it is being exposed to the light from said laser, means for moving individual semiconductor material wafers to and from the position where they are subjected to exposure by said laser light for purposes of detecting surface anomalies, and the necessary signal processing and control circuitry to permit the automated efficient operation of the system.

A significant difference between the present invention and that which went before is the ease of setup and maintenance in that the light incident on the surface to be measured passes directly from laser source to that surface without interception by prisms, reflectors or other optical devices. The elimination of such intermediate optical devices between laser and surface to be measured simplifies the establishment and maintenance of the laser light beam perpendicular to the surface since the troublesome interaction among these optical devices does not present itself in the instant invention.

The laser movement means is unique in that it provides a moveable mounting platform for both the laser source and the scattered light detector and maintains the laser light beam perpendicular to the wafer surface while translating the point of impingement of the light beam on the surface from a spot near the center of the semiconductor wafer to the outer edge of the wafer.

Since mere lateral translation of the laser beam spot from the center to the edge of the wafer would not provide for full surface coverage, a second degree of motion is imparted to the wafer surface. When the surface measurement is to be made, the wafer is held in position by means of a vacuum chuck. The vacuum chuck is designed to hold the semiconductor wafer in position while it is controllably rotated, all the while maintaining the wafer surface perpendicular to the laser light beam. When taken together, the rotary motion imparted to the semiconductor surface by the vacuum chuck plus the lateral translation of the laser beam from center of the wafer to its outer edge provide for full coverage of the semiconductor surface. The laser light beam scans the surface in a pattern which forms an "Archimedes Spiral". With semiconductor wafers as large as five inches in diameter, this spiral scan, surface measurement is accomplished in less than four seconds.

While moving to and from the point at which the surface measurement takes place, the individual wafers are transported on a cushion of inert gas or dry air to preclude contamination of the surfaces by handling in the course of the measurement process.

The invention will best be understood after reading the detailed description which follows in which reference is made to the accompanying illustrations in which:

FIG. 1 is an embodiment of the surface measuring system chosen for illustration in which the reflective surfaces are those of semiconductor wafers of the form normally encountered in semiconductor processing.

FIG. 2 is an exploded view of that portion of the surface measuring system which includes the collimated light source, its movable mount, the airway along which the semiconductor wafers are moved, and the rotary work surface to which the wafer is affixed while the surface measurement is made.

FIG. 3 illustrates the mechanism whereby the carriers in which the wafers are handled are oriented with the airway of the surface measuring system for purposes of unloading and loading said carriers.

FIG. 4 illustrates the motor drive mechanism whereby the collimated light source is laterally translated.

FIG. 5 illustrates the rotary chuck mechanism which is used for holding and rotating the semiconductor wafers during the course of the quality evaluation.

FIG. 6 shows a detail of that portion of FIG. 5 illustrating the manner in which the vacuum is conveyed to the work surface of the rotary chuck.

FIG. 7 illustrates the airway for transporting the semiconductor wafers to the site at which the surface measurement is to be made. Also indicated are the means by which the wafer is located and oriented and placed in position upon the rotary chuck surface.

FIGS. 8 and 9 are sectional views of the airway of FIG. 7 illustrated to impart a clear understanding of the functioning of that device.

FIG. 10 depicts a side view of the airway of FIG. 7 permitting the illustration of mechanical details for stopping the wafer when it reaches the measurement site and for emplacing the wafer on the surface of the vacuum chuck.

FIGS. 11A and B provide a timing diagram illustrating the sequence of operations as a wafer progresses from input to output of the surface measuring system.

FIG. 12 indicates the potential versatility of the measuring system as provision is made to shunt measured wafers to a predetermined one of a multiplicity of wafer loading cassettes as determined by the relative magnitude of surface imperfections found to exist on a given semiconductor wafer.

The generalized concept of a surface inspection system for use in processing semiconductor wafers is depicted in FIG. 1. For transportation to and from the surface measuring equipment, the wafers are handled in cassettes 10. Cassettes 10 which have been loaded with wafers for processing are indicated by the reference numerals 101 and 102 in FIG. 1. Cassettes 10 containing wafers which have passed through the surface inspection cycle are indicated by the reference numerals 103 and 104. The operation of the equipment is such as to sort the wafers in accordance with the magnitude of the measurement of their surface quality. Thus, the surface quality of the wafers in loaded cassette 103 will differ from those within wafer cassette 104, whereas, the wafers within either of these two cassettes will fall within a designated range of measured surface quality. The cassettes are serviced by cassette indexer 11. This involves unloading wafers from loaded cassettes 101 and 102 for purposes of determing surface quality of the semiconductor wafers, and loading the surface inspected wafers into selected cassettes 103 or 104 as determined by the magnitude of the surface quality determined for each individual wafer. Cassettes 10 and cassette indexers 11 are devices well-known in the semiconductor processing arts.

Cassette indexer 11 includes an elevation controlled platform 111 for purposes of raising or lowering cassettes 10 so as to load or unload wafers within said cassette. In the illustration of FIG. 1, a loaded cassette 101 is placed on elevation controlled platform 111 of cassette indexer 11. At this time, elevation controlled platform 111 will be located at its uppermost level. As the belt drive 112 of cassette indexer 11 comes in contact with the lower surface of a wafer within loaded cassette 101, the wafer exits from cassette 101, being transported by belt 112 to be deposited on airway 12 preparatory to having the wafer's surface inspected.

To the right of the illustration of FIG. 1 are shown partially loaded cassettes 103 and 104. When first placed on cassette indexers 11, these cassettes were empty and devoid of any semiconductor wafers. When the empty cassette 10 was placed on elevator platform 111, said platform was at its lowest level limit. In this manner, a wafer emerging from the surface inspection process would be loaded in the topmost position in the cassette.

Cassette indexers 11 are programmed to adjust the height of elevation controlled platform 111 so as to sequentially unload wafers from loaded cassette 101 of FIG. 1, thereby lowering cassette 101 each time a wafer is withdrawn therefrom; and to sequentially load cassette 103 (or 104) as each wafer exits from the surface inspection process, thereby raising cassette 103 each time a wafer is loaded. This function of loading and unloading semiconductor wafer cassettes using cassette indexers is not peculiar to the instant invention and is well known to those familiar with the art.

A novel arrangement of cassettes and cassette indexers is provided in the surface measuring system illustrated in FIG. 1. Although the airway 12 used to transport semiconductor wafers to and from the surface measurement site is a single track device having provision to accept a wafer from only one cassette indexer and the ability to output a wafer to only one indexer, the illustration of FIG. 1 suggests that the system may be used with a multiplicity of cassette indexers located at both the input and the output ends of airway 12. The invention provides a movable base for indexers 11, such that the indexers may be translated laterally so as to align belt 112 of a selected indexer 11 with airway 12. In practice, this means that at the input end of the system when loaded cassette 101, for example, is emptied of wafers, cassettes 101 and 102 will be translated laterally so as to permit the wafers contained in cassette 102 to be unloaded onto airway 12. While cassette 102 is being unloaded, a new full cassette may be used to replace the now empty cassette 101. In this manner, a continuous supply of wafers is presented at the input to airway 12 and no delay is encountered as the result of the emptying of a wafer cassette.

The ability to translate the cassette indexers has additional novel implications. The surface inspection system provides a quantitative measurement of surface quality. That is, the output measurement value is related to some standard. As is typical in quality operations, a range of values centered about a desired standard will usually prove acceptable for the purpose for which the standard was established. Having measured the surface quality of a semiconductor wafer, it is desired that it then be segregated from its companions in terms of its ability to fall within the range of measurement values dictated to be standard or its failure to meet these acceptance criteria. Thus, in FIG. 1, partially loaded cassette 103 may be taken as representative of the destination of those wafers found to be acceptable in terms of their surface quality. Should a wafer fail to pass the surface inspection, partially loaded cassettes 103 and 104 would be laterally translated so as to cause the "defective" wafers to be loaded into partially loaded cassette 104.

Although FIG. 1 illustrates a simple "go, no-go" segregation of wafers at the conclusion of the surface inspection measurement, a more sophisticated means of segregating wafers at the output will be disclosed which will permit the grouping of wafers according to a mutliplicity of predetermined standards.

The means by which the cassette indexers are laterally translated have been designated as reference 13 in the drawings. Throughout the drawings, like reference numbers are used for like components. With respect to FIGS. 1 and 3, the cassette translating mechanism 13 is seen to comprise an air cylinder 131 which provides the necessary motive force to translate the indexers. A swiveled mounting flange 1311 is used to affix air cylinder 131 to support base 14. Slide rails 132, also mounted on base 14, are provided with slide blocks 1321 which are fastened to the undercarriage of indexers 11 so as to support said indexers on said slide rails. The piston arm of air cylinder 131 is connected by means of swivel flange 1312 to the undercarriage of indexers 11. When air cylinder 131 is activated so as to cause its piston arm to extend, indexers 11 will be translated so as to align, for example, loaded cassette 102 with the input of airway 12. When air cylinder 131 is activated so as to cause its piston arm to retract within the cylinder, indexers 11 are translated so as to bring, for example, cassette 101 in line with airway 12. A similar operative statement can be made with respect to partially loaded cassettes 103 and 104 of FIG. 1.

The heart of the surface measuring system is comprised of: 15, which includes the laser light source, scattered light detector, the means for mounting same and maintaining the light beam perpendicular relative to the surface of the wafer, and the translation drive which causes the lateral translation of the laser light source; 12, the airway assembly, which includes a wafer stop for positioning the wafer at the site at which the measurement will be made and a drop track section for lowering the wafer into position upon the work surface of the vacuum chuck assembly 16.

A scattered light detector in the shape of an annulus is mounted to the nose of laser 152. Scattered light detector 151 is mounted such that the nose of laser light source 152 projects through the central opening of the annulus. Laser 152, with detector 151 in place, is mounted to laser platen 153 by means of mounting plate 154. When so mounted, the laser nose and the associated light detector 151 project through a central opening in laser platen 153. Laser platen 153 is supported by ball slide assemblies 155, which in turn are supported above airway 12 by ball slide blocks 156.

A centralized opening in airway 12 accepts the rotary spindle work surface of rotary vacuum chuck assembly 16. Rotary chuck assembly 16 is shown in detail in FIG. 5 and FIG. 6. Chuck assembly 16 is comprised of rotary vacuum spindle work surface 161, spindle shaft 162, bearings 1631; which support spindle shaft 162 in spindle housing 163. A vacuum fitting 1632 is used to communicate a vacuum to work surface 161 via bore 1621. A horizontal bore 1622 in spindle 162, in communion with horizontal bore 1633 in spindle housing 163 completes the vacuum path between vacuum fitting 1632 and work surface 161. Vacuum seals 1634 are used to preserve the vacuum in the vacuum path existing between spindle housing 163 and spindle shaft 162. Vacuum seals 1634 are maintained in position by perforated spacer 1635.

DC servomotor 164 imparts rotary motion to work surface 161 by coupling motor shaft 1641 to spindle shaft 162 by means of shaft coupler 1642. DC servomotor 164 is designed for rapid speed up, open loop operation. Optionally, it may be a hollow rotor motor. The lower end of motor shaft 1641, as oriented in FIG. 5, bears a zero reference. Shaft encoder 165 utilizes this shaft zero reference to provide encoder output signals, at output 1651, which may be used to determine the rotated disposition of work surface 161.

The surface of mounting flange 166 and rotary work surface 161 are machined to run true and prallel to each other. When flange 166 is affixed to the trued surfaces of mounting plate 17 (FIG. 1), the work surface 161 of the rotary vacuum chuck assembly 16 will lie in a plane above and parallel to the surface of mounting plate 17. When airway 12 is mounted to mounting plate 17 by means of mounting blocks 127, rotary vacuum work surface 161 is aligned with a central opening in airway 12 so as to lie just below the travel path of wafers along the said airway. In this way, the wafers may travel down the path of airway 12 without making an interference contact with work surface 161. However, as will be seen when airway 12 is discussed in detail, the clearance maintained between the wafer on the airway and surface 161 is quite small. Mounting plate 17 also provides the support base for laser package 15. A pair of precision ball slides 155 is supported above the air track by means of ball slide blocks 156. Leveling adjustments are provided to assure that the movement of the ball slides is in a plane parallel to the surface of mounting plate 17. Platen 153 bridges the gulf that exists between ball slides 155 and is supported on the upper surfaces of said ball slides. Leveling adjustments are again verified to assure that the surface of laser platen 153 when translated by movement of ball slides 155, moves in a plane which remains parallel to the surface of mounting plate 17. This in turn assures that laser platen 153 will be laterally translated in a plane which is parallel also to rotary work surface 161. The leveling means indicated in the discussion are not illustrated in the figures for the sake of clarity. Means for achieving this leveling funtion will be well known to those versed in the art.

The movement which causes the lateral displacement of platen 153 is communicated by means of a lead screw drive which is coupled to DC steppermotor 157 shown in FIGS. 1, 2, and especially FIG. 4. Lead screw 1571 mates with a lead screw follower assembly on platen 153. This assembly is not shown. A spring damped coupler 1572 joins the shaft of motor 157 with lead screw 1571. A fly wheel 1573 is affixed to the lead screw between the spring damped coupler 1572 and the lead screw follower assembly which is not shown. Since a steppermotor 157 is utilized to provide the lateral translation of laser platen 153, it is possible to track the movement of said platen. For example, assume that lead screw 1571 and its lead screw follower assembly are such as to advance laser platen 153 by 0.0003" per each step of the input drive signal. Assume that the input signal drive is two hundred steps for each revolution of DC steppermotor 157. Then for every two hundred steps at the input of DC steppermotor 157, the motor will complete one revolution of lead screw 1571 and cause the laser platen 153 to be laterally transported 0.006". By knowing the point at which drive is first applied to DC steppermotor 157 and maintaining a count of the number of steps in the input drive signal, the position of laser platen 153 with respect to that point at which drive was first applied will always be known.

A second order damped system is produced by the use of spring damped coupler 1572 and fly wheel 1573. The coupler smooths the effect of the incremental motion of the shaft of steppermotor 157 while fly wheel 1573 reduces the torsional resonance of that motor.

Laser 152 with scattered light detector 151 mounted on its nose is affixed to laser platen 153 by means of laser mounting plate 154. An opening in laser platen 153 permits the passage of a beam of laser light from laser 152. Adjustments, not shown, are provided to establish the laser beam on a path perpendicular to the surface of laser platen 153. Adjustments for this function are well known in the art. Establishing the laser light beam on a path perpendicular to laser platen 153 effectively causes the light beam to strike work surface 161 at an incidence angle of ninety degrees. With the beam established at ninety degrees to work surface 161 plus the ability to translate that beam while work surface 161 is rotated, the stage is set for the scattered light inspection of the surface of a semiconductor wafer.

Reference should now be made to the sheet containing FIGS. 7 through 10 inclusive. Airway 12 and parts thereof are illustrated in this group of Figures. FIG. 9 is a cross-sectional view taken as indicated in FIG. 7. Although the word "air" will be used in description of airway 12, it should be borne in mind that any appropriate gaseous medium such as dry air or an inert gas may effectively be used to transport the semiconductor wafer.

In FIG. 7, it is seen that air vents 121 located in a top surface of airway 12 form two parallel rows which effectively define an airtrack down which a semiconductor wafer may travel. In the cross-sectional view of FIG. 9, it is seen that airway 12 is constructed so as to define an air plenum 1211. A supply of air to said plenum is introduced at air input 1212. Air introduced at input 1212 fills plenum 1211 and exits therefrom by flowing out vents 121. This flow of air out vents 121, is sufficient to support a semiconductor wafer between side walls 1213 which further define the airtrack down which said semiconductor wafers travel on airway 12. Airway 12 is comprised of three sections as illustrated in FIGS. 7 and 10: a left-hand fixed section 122; a central, movable, drop track section 123; and a right-hand fixed section 124. In transiting airway 12, a wafer will enter at the left side of airway section 122, travel across central section 123, and exit at the right-hand edge of section 124. As may be seen in cross-sectional view FIG. 8, the flow of air from plenum 1211 out air vents 121 is directed such as to cause the air to flow from left to right along the airtrack of airway 12 in the illustration of FIG. 7. It is this left to right flow which supports the wafer and transports it along the airway defined by the multiplicity of vents 121 and side edges 1213.

A semiconductor wafer entering airway section 122 will be transported on the airtrack until it is detected at sensor 1221. When the presence of the wafer is detected by sensor 1221, vacuum stop 1222 is activated. The effect of activating stop 1222 is to halt the movement of a wafer across the airtrack of airway 12. While the wafer is held fixed by said vacuum stop sensor 1221 alerts the system controls that a wafer is awaiting processing. The wafer will be held at vacuum stop 1222 until the system ascertains that there is a clear track ahead. With a clear track ahead, vacuum stop 1222 is then inactivated and the wafer proceeds on its journey to the right until it is brought to a halt by wafer stop 1231.

With its travel halted by wafer stop 1231, the wafer is positioned above a central opening 1232 in airway 12. While so positioned, it is supported on the flow of air exiting from vents 121. In the assembled surface inspection system, rotary work surface 161 is positioned in central opening 1232 of airway 12 such that a wafer may progress along the airtrack just avoiding interfering contact with the work surface 161. Thus, with wafer stop 1231 positioned so as to impede the progress of the wafer down the airtrack of airway 12, the wafer will be held in position directly above the work surface 161.

Once a wafer has been released by vacuum stop 1222, sufficient time is permitted to allow the wafer to travel along section 123 so as to reach wafer stop 1231 and to settle down into stable contact with said wafer stop. When sufficient time has elapsed to cause the settling of a wafer against wafer stop 1231, a vacuum is communicated to rotary work surface 161. Section 123 of airway 12 is then caused to move in such a manner as to lower the wafer into intimate contact with work surface 161 where the wafer becomes readily affixed by reason of the vacuum communicated to that surface. Wafer stop 1231 is then moved so that it no longer makes an interference contact with the edge of the wafer.

To understand how the motion is imparted to both section 123 of airway 12 and to wafer stop 1231, reference should be made to FIGS. 7 and 10. Here it may first be noted that drop track section 123 is supported by pivot rod 1233. It is maintained in this position by the action of drop track cylinder 1235 which is shown in FIG. 10 as having its fixed end supported to the undercarriage of fixed section 124 of airway 12 while its piston arm is affixed by a clevis arrangement to the undercarriage of drop track section 123. Retraction of the piston arm of air cylinder 1235 will cause drop track section 123 to pivot about pivot rod 1233 in a counter-clockwise direction such that the left-hand end of section 123 is lowered. A set screw 1223 and stop bracket 1237 arrangement permits the drop track to have its surfaces adjusted to be flush with the associated surfaces of fixed section 122 when air cylinder 1235 is activated so as to extend its piston arm and thereby raise the left-hand end of drop section 123.

A similar pivot rod 1234 is provided, in cooperation with wafer stop arm 1238, to raise and lower wafer stop 1231. Motion is imparted to wafer 1231 by operation of air cylinder 1236. The fixed end of air cylinder 1236 is fastened to the undercarriage of drop track section 123. The piston arm of air cylinder 1236 is fastened to wafer stop 1238 by means of a clevis arrangement. Operating wafer stop cylinder 1236 so as to cause the retraction of the piston arm causes the lowering of wafer stop 1231 as it is forced to pivot counter-clockwise about pivot rod 1234. Although in its raised position wafer stop 1231 will make contact with a wafer traveling along the airtrack of airway 12; lowering wafer stop 1231 will remove that contact.

With the drop track lowered, the vacuum on vacuum chuck assembly 16, a wafer in intimate contact with the work surface 161 and affixed there by the vacuum, and finally with the wafer stop arm 1231 retracted, the wafer is free to be rotated with rotary work surface 161.

Semiconductor wafers, while generally circular, typically have one or more segments removed so as to produce what is known as a flat along some portion of its curved outer edge. It is possible to use this edge to obtain a reference position on the surface of the wafer as it is rotated by rotary work surface 161. To this end, wafer-flat sensor 1224 is suggested in FIG. 7 for the purpose of detecting the discontinuity introduced by the flat in the smooth, continuous curve at the periphery of the wafer.

At the point in time we have now reached in our discussion of the transit of airway 12 by a semiconductor wafer, DC servomotor 164 will be energized. This will cause the rapid rotary acceleration of work surface 161. At the same time, drive signals will be applied to steppermotor 157 so as to cause the laser beam, which is now functioning, to transit across the surface of the wafer undergoing surface inspection. By properly establishing the initial position of the laser, the laser beam will transit across the face of the wafer reaching the center of the wafer at the time that servomotor 164, and therefore work surface 161, has reached its maximum rotary acceleration. From that time, the output of scattered light detector 151 is determined and correlated with the rotated position of the semiconductor wafer under test and the translated position of the laser beam. By correlating these readings with respect to the location of the flat at the edge of the semiconductor wafer as determined by wafer-flat sensor 1224, the actual location of surface anomalies may be pinpointed on the wafer.

With the surface inspection of that particular wafer completed, the drive to the rotary work surface 161 is discontinued, the vacuum supply to that work surface is terminated and drop track section 123 is moved to its raised position thereby floating the wafer from rotary surface 161 on the flow of air exiting from air vents 121. Wafer stop 1231 is maintained in its depressed position and the wafer is, therefore, free to travel unimpeded to the right along the airtrack of airway 12. As the wafer traverses the fixed section 124 of airway 12, its exit therefrom is sensed by clear-track sensor 1241. With the track clear, wafer stop 1231 is again moved to its raised position and a new wafer, which may be awaiting tests at vacuum stop 1222, is released to travel down until impeded by wafer stop 1231. The test cycle then repeats itself.

The test cycle may be readily understood by referring to FIGS. 11A and 11B. In FIG. 11A, the various steps of each cycle and their timing are spelled out. In FIG. 11B, three wafers are shown being cycled along the airtrack of airway 12. The movement of each of these wafers; W0, W1, and W2; along the airtrack of airway 12 may be correlated by their relative position with respect to the timing diagram of FIG. 11A.

The arrangement of cassettes 103 and 104 at the output of airway 12 provides a simple go, no-go segregation of tested wafer surfaces. FIG. 12 suggests that the inclusion of an additional airway section, eg. 125 between output cassettes 103 and 104, permits the addition of other output cassettes: 105, 106, 107 . . . 10n; each pair of cassettes having an airway section 126, 127 . . . 12n, associated. In this manner, the inspected wafers may be segregated with a finer granularity with respect to the measured surface quality.

When a wafer is measured and its surface quality determined, the output cassette, eg 105, associated with that determined surface quality will be laterally translated so as to be in-line to receive the wafer as it exits from the measuring process.

Although the output cassettes are shown arranged in pairs no limitation is implied thereby and other arrangements may be employed.

What we have disclosed is a surface measuring system which uses light scattered from surface anomalies to profide a quantitative measurement of surface quality. Because the collimated light travels from light source to the surface to be measured without impinging upon reflective surfaces, prisms, or other optical devices to bend or deflect its path, the system is relatively easy to set up and maintain. The means by which the collimated light beam is moved across the surface undergoing measurement is such as to provide full coverage of the surface and to permit correlation of the beam location on that surface with the sensed indication of surface anomalies. The physical system has been described without indication of signal processing or control circuitry which those familiar with the art will be well familiar with, knowing that various position sensors indicated in the foregoing disclosure are required as well as sensors for indexing the initial and final positions of the laser light beam. The rotary drive motor is a stepperdrive motor and the method of determining the rotated position of the disc has been set forth in the foregoing discussion. Means for sampling the output of the scattered light detector with reference to the determined position of the light beam are well known. While such processing and control circuitry may in themselves be innovative to the point of patentable, it is not necessary that such unique circuitry be employed in practicing the invention disclosed herein.

Having described our invention in such clear terms as to enable those skilled in the art to understand and to practice it, that which we claim as worthy of the grant of Letters Patent is:

1. A scattered light surface measuring system for the detection of surface anomalies on reflective surfaces of flat articles to be tested, comprising:
    a support having a horizontal upper surface to support a flat test article with its upper reflective surface in a horizontal position;
    a collimated light light source mounted above the support and positioned and arranged to transmit a collimated light beam directly perpendicularly upon the horizontal reflective surface in the absence of interception by reflectors, prisms, lenses, or other optical path bending devices;
    a scattered light detector surrounding the collimated light beam above the support to intercept the light rays scattered by the surface anomalies of the test article;
    the support for the test article is controllably powered to rotate continuously about a vertical axis as required;
    the light source is mounted to travel transversely over the support and test article while maintaining the perpendicularity of the collimated light beam to the surface of the test articles;
    controllable power means is provided to produce the transverse travel of the light source;
    and the control means are operable to cause simultaneous rotation of the test sample and transverse travel of the light source between the center and the perimeter of the test article and produce impingement of the light beam upon the entire area of the test sample in the form of an Archimedean spiral; and
    the support for the test article has a perforated upper surface and a controllable vacuum pump is connected thereto through the interior of the support to constitute a vacuum chuck for holding the test article securely in place while the chuck is stationary or rotating.

2. A scattered light surface measuring system for the detector of surface anomalies on reflective surfaces of flat articles to be tested, comprising:
    a support having a horizontal upper surface to support a flat test article with its upper reflective surface in a horizontal position;
    a collimated light light source mounted above the support and positioned and arranged to transmit a collimated light beam directly perpendicularly upon the horizontal reflective surface in the absence of interception by reflectors, prisms, lenses, or other optical path bending devices;
    and a scattered light detector surrounding the collimated light beam above the support to intercept the light rays scattered by the surface anomalies of the test article;
    the support for the test article is controllably powered to rotate continuously about a vertical axis as required;
    the light source is mounted to travel transversely over the support and test article while maintaining the perpendicularity of the collimate light beam to the surface of the test articles;
    controllable power means is provided to produce the transverse travel of the light source;
    the control means are operable to cause simultaneous rotation of the test sample and transverse travel of the light source between the center and the perimeter of the test article and produce impingement of the light beam upon the entire area of the test sample in the form of an Archimedean spiral;
    loading means are provided for moving successive test articles from a storage location to the vicinity of the rotatable support for test;
    unloading means are provided for moving the articles from the test location to a second storage location;
    the loading and unloading means include an air track provided with jet means for conveying the articles along the track;
    an intermediate section of the track is formed with an aperture located above the rotary support at the test location;
    stop means is mounted on the track to intercept each article above the aperture;

the intermediate section of the track is vertically movable with respect to the other sections; and means are provided to lower the track and deposit a test article on the rotary support for the test operation free of interference by other parts of the apparatus.

3. The measuring system of claim 2 said loading means further comprising:

input cassette means having at least an input cassette for housing an uninspected plurality of said test articles; and input indexing means for selectively shifting a selected one of said uninspected plurality of said test articles onto said track.

4. The measuring system of claim 2 said unloading means comprising:

lifting means for raising said portion of said track so that said test articles is thereby lifted from said rotary work surface; and release means for removing the impediment of said stop means so that said jet means can further propel said test article along said track.

5. A scattered light surface measuring system for the detection of surface anomalies on reflective surfaces of flat articles to be tested, comprising:

a support having a horizontal upper surface to support a flat test article with its upper reflective surface in a horizontal position;

a collimated light light source mounted above the support and positioned and arranged to transmit a collimated light beam directly perpendicularly upon the horizontal reflective surface in the absence of interception by reflectors, prisms, lenses, or other optical path bending devices;

and a scattered light detector surrounding the collimated light beam above the support to intercept the light rays scattered by the surface anomalies of the test article;

said scattered light detector has an annular shape and further has a disposition about said beam of collimated light so that said beam of collimated light passes undetected through the center of the annulus while reflected light scattered by a surface anomaly is detected.

* * * * *